(12) United States Patent
McConnell et al.

(10) Patent No.: US 11,672,946 B2
(45) Date of Patent: Jun. 13, 2023

(54) PROTECTION AND ACTUATION MECHANISM FOR CONTROLLED RELEASE OF IMPLANTABLE EMBOLIC DEVICES

(71) Applicant: BOSTON SCIENTIFIC SCIMED, INC., Maple Grove, MN (US)

(72) Inventors: Kevin McConnell, Minneapolis, MN (US); Nicholas Lee Tassoni, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 298 days.

(21) Appl. No.: 17/027,056

(22) Filed: Sep. 21, 2020

(65) Prior Publication Data

US 2021/0085918 A1 Mar. 25, 2021

Related U.S. Application Data

(60) Provisional application No. 62/904,872, filed on Sep. 24, 2019.

(51) Int. Cl.
*A61B 17/12* (2006.01)
*A61M 25/00* (2006.01)
(Continued)

(52) U.S. Cl.
CPC .... *A61M 25/0021* (2013.01); *A61M 25/0138* (2013.01); *A61M 25/0147* (2013.01);
(Continued)

(58) Field of Classification Search
CPC ........ A61B 17/1214; A61B 2017/1205; A61B 2017/12054; A61B 2017/12059;
(Continued)

(56) References Cited

U.S. PATENT DOCUMENTS

| 3,342,179 A | 9/1967 | Ellman |
|---|---|---|
| 5,117,839 A | 6/1992 | Dance |

(Continued)

FOREIGN PATENT DOCUMENTS

| EP | 1621149 A1 | 2/2006 |
|---|---|---|
| EP | 1728478 A1 | 12/2006 |

(Continued)

OTHER PUBLICATIONS

International Search Report and Written Opinion dated Jun. 15, 2018 for International Application No. PCT/US2018/021978.

(Continued)

*Primary Examiner* — Kathleen S Holwerda
(74) *Attorney, Agent, or Firm* — Seager, Tufte & Wickhem LLP

(57) ABSTRACT

A medical device system may include an elongate shaft having a lumen extending to a distal end of the elongate shaft, wherein a proximal portion of the elongate shaft is configured to disengage from a distal portion of the elongate shaft; a medical device disposed proximate the distal end of the elongate shaft; a release wire disposed within the lumen of the elongate shaft, wherein the release wire releasably attaches the medical device to the distal end of the elongate shaft; and an introducer sheath slidably disposed over the elongate shaft, wherein the introducer sheath is configured to disengage the proximal portion of the elongate shaft from the distal portion of the elongate shaft.

16 Claims, 10 Drawing Sheets

(51) Int. Cl.
*A61M 25/01* (2006.01)
*A61F 2/966* (2013.01)
*A61B 17/00* (2006.01)
*A61F 2/24* (2006.01)
*A61F 2/01* (2006.01)

(52) U.S. Cl.
CPC ..... *A61B 17/1214* (2013.01); *A61B 17/12113* (2013.01); *A61B 2017/00867* (2013.01); *A61B 2017/12054* (2013.01); *A61F 2/011* (2020.05); *A61F 2/2439* (2013.01); *A61F 2/966* (2013.01); *A61M 2025/0042* (2013.01)

(58) Field of Classification Search
CPC ........... A61B 2017/12063; A61B 2017/12068; A61B 2017/12072; A61B 2017/12077; A61B 2017/12081; A61B 2017/12086; A61B 2017/1209; A61B 2017/01295; A61F 2/95–2/97; A61M 25/0021; A61M 25/0138; A61M 25/0147; A61M 2025/0042
See application file for complete search history.

(56) References Cited

U.S. PATENT DOCUMENTS

| | | |
|---|---|---|
| 5,234,437 A | 8/1993 | Sepetka |
| 5,250,071 A | 10/1993 | Palermo |
| 5,282,478 A | 2/1994 | Fleischhaker et al. |
| 5,304,195 A | 4/1994 | Twyford et al. |
| 5,312,415 A | 5/1994 | Palermo |
| 5,546,958 A | 8/1996 | Thorud et al. |
| 5,925,059 A | 7/1999 | Palermo et al. |
| RE37,117 E | 3/2001 | Palermo |
| 6,277,125 B1 | 8/2001 | Barry et al. |
| 6,491,646 B1 | 12/2002 | Blackledge |
| 7,044,134 B2 | 5/2006 | Khairkhahan et al. |
| 7,074,134 B2 | 7/2006 | Piche |
| 7,708,755 B2 | 5/2010 | Davis, III et al. |
| 7,815,661 B2 | 10/2010 | Mirizzi et al. |
| 7,896,899 B2 | 3/2011 | Patterson et al. |
| 8,142,456 B2 | 3/2012 | Rosqueta et al. |
| 8,236,042 B2 | 8/2012 | Berez et al. |
| 8,333,786 B2 | 12/2012 | Mirizzi et al. |
| 8,333,796 B2 | 12/2012 | Tompkins et al. |
| 8,568,416 B2 | 10/2013 | Schmitz et al. |
| 8,641,777 B2 | 2/2014 | Strauss et al. |
| 8,696,701 B2 | 4/2014 | Becking et al. |
| 8,747,597 B2 | 6/2014 | Rosqueta et al. |
| 8,795,313 B2 | 8/2014 | Liang et al. |
| 8,801,746 B1 | 8/2014 | Kreidler et al. |
| 8,911,487 B2 | 12/2014 | Bennett et al. |
| 9,017,350 B2 | 4/2015 | Karabey et al. |
| 9,017,361 B2 | 4/2015 | Karabey et al. |
| 9,060,773 B2 | 6/2015 | Nguyen et al. |
| 9,119,948 B2 | 9/2015 | Lee et al. |
| 9,186,151 B2 | 11/2015 | Tompkins et al. |
| 9,198,670 B2 | 12/2015 | Hewitt et al. |
| 9,301,827 B2 | 4/2016 | Strauss et al. |
| 9,307,999 B2 | 4/2016 | Li et al. |
| 9,320,618 B2 | 4/2016 | Schmitz et al. |
| 9,468,442 B2 | 10/2016 | Huynh et al. |
| 9,498,226 B2 | 11/2016 | Cage et al. |
| 9,549,740 B2 | 1/2017 | Rees |
| 9,554,805 B2 | 1/2017 | Tompkins et al. |
| 9,700,322 B2 | 7/2017 | Dias et al. |
| 2002/0022800 A1 | 2/2002 | O'Holloran et al. |
| 2005/0119675 A1 | 6/2005 | Adams et al. |
| 2006/0036281 A1 | 2/2006 | Patterson et al. |
| 2006/0212055 A1 | 9/2006 | Karabey et al. |
| 2006/0229669 A1 | 10/2006 | Mirizzi et al. |
| 2006/0282159 A1 | 12/2006 | Taheri |
| 2007/0083219 A1 | 4/2007 | Buiser et al. |
| 2007/0083226 A1 | 4/2007 | Buiser et al. |
| 2007/0135826 A1 | 6/2007 | Zaver et al. |
| 2007/0186933 A1 | 8/2007 | Domingo et al. |
| 2007/0208276 A1 | 9/2007 | Volk et al. |
| 2007/0270903 A1 | 11/2007 | Davis, III et al. |
| 2007/0282373 A1 | 12/2007 | Ashby et al. |
| 2007/0293928 A1 | 12/2007 | Tomlin |
| 2008/0109059 A1 | 5/2008 | Gordon et al. |
| 2008/0119891 A1 | 5/2008 | Miles et al. |
| 2008/0269719 A1* | 10/2008 | Balgobin ........... A61B 17/1214 604/28 |
| 2008/0275458 A1 | 11/2008 | Bleich et al. |
| 2008/0300616 A1 | 12/2008 | Que et al. |
| 2009/0043331 A1 | 2/2009 | Buiser et al. |
| 2009/0062838 A1 | 3/2009 | Brumleve et al. |
| 2009/0062845 A1 | 3/2009 | Tekulve |
| 2009/0125059 A1 | 5/2009 | Verzal et al. |
| 2009/0163934 A1 | 6/2009 | Raschdorf, Jr. et al. |
| 2009/0177261 A1 | 7/2009 | Teoh et al. |
| 2009/0270877 A1* | 10/2009 | Johnson ................... A61F 2/95 606/108 |
| 2009/0270978 A1 | 10/2009 | Virkler et al. |
| 2009/0287291 A1 | 11/2009 | Becking et al. |
| 2009/0287294 A1 | 11/2009 | Rosqueta et al. |
| 2010/0106178 A1 | 4/2010 | Obermiller et al. |
| 2010/0121350 A1 | 5/2010 | Mirigian |
| 2010/0174269 A1 | 7/2010 | Tompkins et al. |
| 2011/0046657 A1 | 2/2011 | Guo et al. |
| 2011/0166588 A1 | 7/2011 | Connor et al. |
| 2011/0184454 A1 | 7/2011 | Barry et al. |
| 2011/0202085 A1 | 8/2011 | Loganathan et al. |
| 2011/0238147 A1 | 9/2011 | Bennett et al. |
| 2011/0265943 A1 | 11/2011 | Rosqueta et al. |
| 2011/0319926 A1 | 12/2011 | Becking et al. |
| 2012/0041470 A1 | 2/2012 | Shrivastava et al. |
| 2012/0046687 A1 | 2/2012 | Trommeter et al. |
| 2012/0177436 A1 | 7/2012 | LaBombard |
| 2012/0197299 A1 | 8/2012 | Fabian, Jr. |
| 2012/0203322 A1 | 8/2012 | Eells |
| 2012/0283812 A1 | 11/2012 | Lagodzki et al. |
| 2012/0316597 A1 | 12/2012 | Fitz et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066360 A1 | 3/2013 | Becking et al. |
| 2013/0072961 A1 | 3/2013 | Cage et al. |
| 2013/0085520 A1 | 4/2013 | Liang et al. |
| 2013/0085522 A1 | 4/2013 | Becking et al. |
| 2013/0152941 A1 | 6/2013 | Nguyen et al. |
| 2013/0253572 A1 | 9/2013 | Molaei et al. |
| 2013/0261730 A1 | 10/2013 | Bose et al. |
| 2013/0296917 A1 | 11/2013 | Rees |
| 2013/0331882 A1 | 12/2013 | Tompkins et al. |
| 2014/0058434 A1 | 2/2014 | Jones et al. |
| 2014/0058435 A1 | 2/2014 | Jones et al. |
| 2014/0128907 A1 | 5/2014 | Hui et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0148843 A1 | 5/2014 | Strauss et al. |
| 2014/0172001 A1 | 6/2014 | Becking et al. |
| 2014/0236127 A1 | 8/2014 | Lee et al. |
| 2014/0277078 A1 | 9/2014 | Slazas et al. |
| 2014/0358175 A1 | 12/2014 | Tompkins et al. |
| 2015/0005807 A1 | 1/2015 | Lagodzki et al. |
| 2015/0073524 A1 | 3/2015 | Bennett et al. |
| 2015/0112378 A1 | 4/2015 | Torp |
| 2015/0142049 A1 | 5/2015 | Delgado et al. |
| 2015/0157332 A1 | 6/2015 | Obermiller et al. |
| 2015/0196304 A1 | 7/2015 | Rabkin et al. |
| 2015/0230802 A1 | 8/2015 | Lagodzki et al. |
| 2015/0250470 A1 | 9/2015 | Vargas |
| 2015/0257763 A1 | 9/2015 | Blum et al. |
| 2015/0272589 A1 | 10/2015 | Lorenzo |
| 2015/0297240 A1 | 10/2015 | Divino et al. |
| 2015/0327868 A1 | 11/2015 | Islak et al. |
| 2015/0335333 A1 | 11/2015 | Jones et al. |
| 2015/0342611 A1 | 12/2015 | Leoplod et al. |
| 2015/0343181 A1 | 12/2015 | Bradway et al. |

(56) References Cited

U.S. PATENT DOCUMENTS

| | | |
|---|---|---|
| 2016/0008003 A1 | 1/2016 | Kleshinski et al. |
| 2016/0022445 A1 | 1/2016 | Ruvalcaba et al. |
| 2016/0030052 A1 | 2/2016 | Cragg et al. |
| 2016/0113657 A1 | 4/2016 | Mathis et al. |
| 2016/0166257 A1 | 6/2016 | Allen et al. |
| 2016/0192942 A1 | 7/2016 | Strauss et al. |
| 2016/0228123 A1 | 8/2016 | Anderson et al. |
| 2016/0228124 A1 | 8/2016 | Trommeter et al. |
| 2016/0228128 A1 | 8/2016 | Connolly |
| 2016/0317274 A1 | 11/2016 | Liu et al. |
| 2017/0224350 A1 | 8/2017 | Shimizu et al. |
| 2018/0133435 A1 | 5/2018 | Pederson, Jr. et al. |
| 2018/0228493 A1 | 8/2018 | Aguilar et al. |
| 2019/0105055 A1 | 4/2019 | Cao et al. |
| 2020/0187951 A1* | 6/2020 | Blumenstyk ..... A61B 17/12113 |
| 2020/0229957 A1 | 7/2020 | Bardsley et al. |

FOREIGN PATENT DOCUMENTS

| | | |
|---|---|---|
| EP | 2213244 A1 | 8/2010 |
| EP | 1441649 B1 | 8/2011 |
| EP | 2777542 A2 | 9/2014 |
| EP | 2777545 A2 | 9/2014 |
| EP | 3085310 A1 | 10/2016 |
| JP | H10192290 A | 7/1998 |
| JP | 2016537134 A | 12/2016 |
| WO | 0232496 A1 | 4/2002 |
| WO | 03032818 A2 | 4/2003 |
| WO | 03075997 A1 | 9/2003 |
| WO | 2007047111 A1 | 4/2007 |
| WO | 2007070797 A2 | 6/2007 |
| WO | 2010030993 A1 | 3/2010 |
| WO | 2010098804 A1 | 9/2010 |
| WO | 2014145012 A2 | 9/2014 |
| WO | 2014145005 A3 | 4/2015 |
| WO | 2015134758 A1 | 9/2015 |
| WO | 2016044647 A2 | 3/2016 |
| WO | 2017192394 A1 | 11/2017 |

OTHER PUBLICATIONS

International Search Report and Written Opinion dated Feb. 26, 2018 for International Application No. PCT/US2017/061779.
International Search Report and Written Opinion dated Jul. 13, 2018 for International Application No. PCT/US2018/028240.
International Search Report and Written Opinion dated Dec. 5, 2018 for International Application No. PCT/US2018/000148.
International Search Report and Written Opinion dated Apr. 5, 2019 for International Application No. PCT/US2019/016245.
International Search Report and Written Opinion dated Jul. 1, 2020 for International Application No. PCT/US2020/021428.
International Preliminary Report on Patentability for PCT Application No. PCT/US2017/061779 dated May 31, 2019, 7 pages.
International Search Report and Written Opinion dated Nov. 10, 2020 for International Application No. PCT/US2020/051968.

* cited by examiner

US 11,672,946 B2

PROTECTION AND ACTUATION MECHANISM FOR CONTROLLED RELEASE OF IMPLANTABLE EMBOLIC DEVICES

CROSS-REFERENCE TO RELATED APPLICATIONS

This application claims the benefit of priority of U.S. Provisional Application No. 62/904,872 filed Sep. 24, 2019, the entire disclosure of which is hereby incorporated by reference.

TECHNICAL FIELD

The present disclosure pertains to medical devices and methods for manufacturing and/or using medical devices. More particularly, the present disclosure pertains to configurations of a system for releasing for medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a medical device system may comprise an elongate shaft having a lumen extending to a distal end of the elongate shaft; a medical device disposed proximate the distal end of the elongate shaft; a release wire disposed within the lumen of the elongate shaft, wherein the release wire releasably attaches the medical device to the distal end of the elongate shaft; and an introducer sheath slidably disposed over the elongate shaft. A proximal portion of the elongate shaft may be configured to disengage from a distal portion of the elongate shaft. The introducer sheath may be configured to disengage the proximal portion of the elongate shaft from the distal portion of the elongate shaft.

In addition or alternatively, the proximal portion of the elongate shaft is fixedly attached to a proximal end of the release wire.

In addition or alternatively, disengaging the proximal portion of the elongate shaft from the distal portion of the elongate shaft permits the release wire to axially translate relative to the elongate shaft.

In addition or alternatively, axial translation of the proximal portion of the elongate shaft relative to the distal portion of the elongate shaft releases the medical device from the distal end of the elongate shaft.

In addition or alternatively, the proximal portion of the elongate shaft is integrally formed with the distal portion of the elongate shaft.

In addition or alternatively, the elongate shaft includes a pre-defined break region formed in a wall of the elongate shaft.

In addition or alternatively, the proximal portion of the elongate shaft is disposed proximal of the pre-defined break region and the distal portion of the elongate shaft is disposed distal of the pre-defined break region.

In addition or alternatively, the pre-defined break region includes a plurality of slits formed in the wall of the elongate shaft.

In addition or alternatively, the elongate shaft includes a stop feature disposed proximate a proximal end of the elongate shaft. The introducer sheath includes a necked region configured to engage the stop feature with the pre-defined break region disposed between a proximal end of the introducer sheath and a distal end of the introducer sheath.

In addition or alternatively, the introducer sheath includes a stepped region configured to engage the stop feature with the pre-defined break region disposed at the distal end of the introducer sheath.

In addition or alternatively, a medical device system may comprise an elongate shaft having a lumen extending to a distal end of the elongate shaft, wherein a proximal portion of the elongate shaft is configured to disengage from a distal portion of the elongate shaft; a medical device disposed proximate the distal end of the elongate shaft; a release wire disposed within the lumen of the elongate shaft, wherein the release wire releasably attaches the medical device to the distal end of the elongate shaft; wherein the release wire is fixedly attached to the proximal portion of the elongate shaft; an introducer sheath slidably disposed over the elongate shaft, wherein the introducer sheath is configured to disengage the proximal portion of the elongate shaft from the distal portion of the elongate shaft; and a microcatheter configured to deliver the medical device to a treatment site, wherein the introducer sheath is configured to guide the medical device and the elongate shaft into a lumen of the microcatheter.

In addition or alternatively, a distal end of the introducer sheath is configured to be disposed within a proximal end of the lumen of the microcatheter.

In addition or alternatively, the proximal portion of the elongate shaft includes a stop feature.

In addition or alternatively, the introducer sheath includes a proximal portion and a distal portion. The proximal portion of the introducer sheath includes a lumen having a radial extent greater than a radial extent of the stop feature. The distal portion of the introducer sheath includes a lumen having a radial extent less than the radial extent of the stop feature.

In addition or alternatively, the proximal portion of the introducer sheath is joined to the distal portion of the introducer sheath at a stepped region.

In addition or alternatively, the proximal portion of the introducer sheath includes a necked region having a radial extent less than the radial extent of the lumen of the proximal region of the introducer sheath.

In addition or alternatively, the radial extent of the necked region is less than the radial extent of the stop feature.

In addition or alternatively, a medical device system may comprise an elongate shaft including a pre-defined break region located along a length of the elongate shaft, the pre-defined break region separating a proximal portion of the elongate shaft from a distal portion of the elongate shaft; wherein the proximal portion of the elongate shaft is formed with the distal portion of the elongate shaft as a unitary structure; a medical device disposed proximate a distal end of the elongate shaft; a release wire disposed within the elongate shaft, wherein the release wire is configured to releasably attach the medical device to the elongate shaft in a first position; wherein the proximal portion of the elongate shaft is fixedly attached to a proximal end of the release wire; and an introducer sheath slidably disposed over the elongate shaft, wherein the introducer sheath is configured to disengage the proximal portion of the elongate shaft from the distal portion of the elongate shaft.

In addition or alternatively, the release wire is translatable to a second position when the distal portion of the elongate shaft is disengaged from the proximal portion of the elongate shaft. In the second position, the medical device is detachable from the distal end of the elongate shaft.

In addition or alternatively, at a proximal-most position of the introducer sheath relative to the elongate shaft, a distal end of the introducer sheath is disposed at the pre-defined break region. Deflection of the introducer sheath relative to a central longitudinal axis of the elongate shaft at the proximal-most position induces disengagement of the proximal portion of the elongate shaft from the distal portion of the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
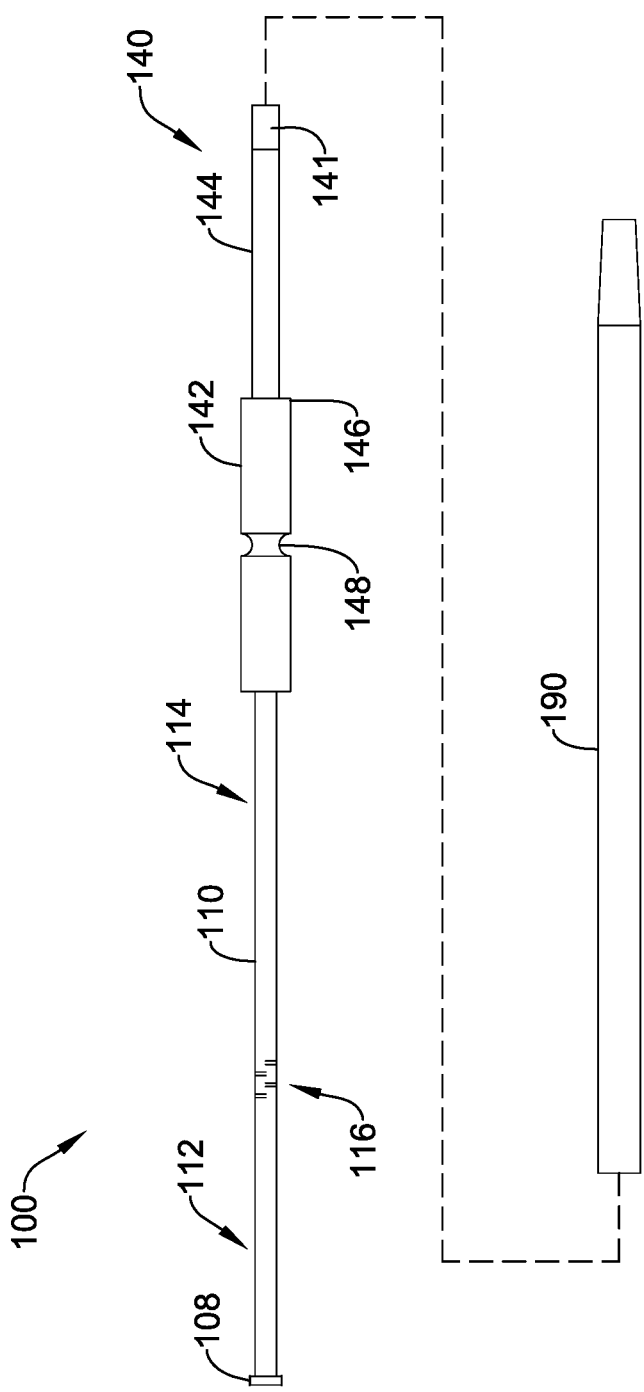
FIG. 1 illustrates aspects of a medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 2:
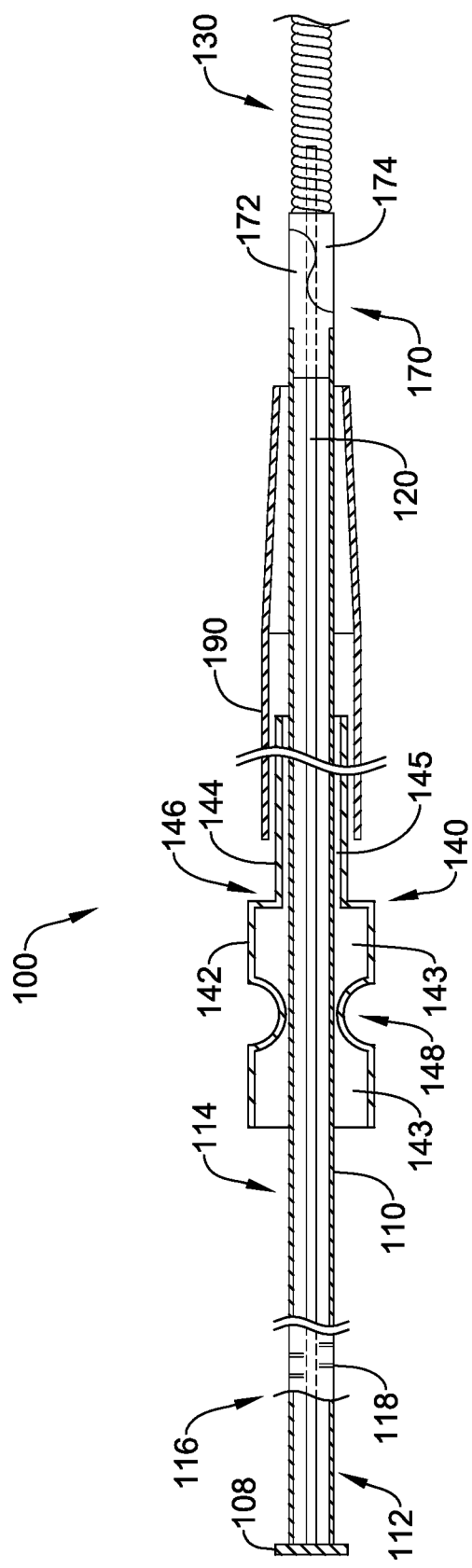
FIGS. 2-4 are partial cross-sectional views illustrating aspects of using the medical device system to deliver a medical device.

FIGS. 1 and 2 illustrate aspects of a medical device system 100. The medical device system 100 may include an elongate shaft 110 having a lumen extending from a proximal end of the elongate shaft 110 to a distal end of the elongate shaft 110. In some embodiments, the elongate shaft 110 may be a catheter, a hypotube, or other similar tubular and/or annular structure defined by a wall having an inner surface and an outer surface. In some embodiments, the elongate shaft 110 may have a constant and/or uniform outer extent and/or outer diameter along its entire length. Other configurations, including but not limited to the elongate shaft 110 having one or more tapers, steps, and/or changes in outer extent and/or outer diameter, are also contemplated. Some suitable but non-limiting materials for the elongate shaft 110, for example metallic materials, polymer materials, composite materials, etc., are described below.

The elongate shaft 110 may include a proximal portion 112, a distal portion 114, and a pre-defined break region 116 located along a length of the elongate shaft 110, the pre-defined break region 116 separating the proximal portion 112 of the elongate shaft 110 from the distal portion 114 of the elongate shaft 110. The proximal portion 112 of the elongate shaft 110 may be disposed proximal of the pre-defined break region 116 and the distal portion 114 of the elongate shaft 110 may be disposed distal of the pre-defined break region 116. In some embodiments, the proximal portion 112 of the elongate shaft 110 may be integrally formed with the distal portion 114 of the elongate shaft 110 as a unitary structure. The pre-defined break region 116 may be formed in the wall of the elongate shaft 110. In at least some embodiments, the pre-defined break region 116 may include a plurality of slits 118 formed in the wall of the elongate shaft 110. Other configurations are also contemplated. For example, the pre-defined break region 116 may include a perforation, a plurality of apertures extending through the wall of the elongate shaft 110, a thinned or weakened feature or features formed in the wall of the elongate shaft 110, etc. The proximal portion 112 of the elongate shaft 110 may be configured to disengage from the distal portion 114 of the elongate shaft 110 at the pre-defined break region 116, as discussed herein. However, regardless of form, the pre-defined break region 116 may generally be strong enough to avoid and/or prevent accidental or unintended disengagement of the proximal portion 112 of the elongate shaft 110 from the distal portion 114 of the elongate shaft 110 through normal use and/or handling of the medical device system 100 and/or the elongate shaft 110.

The elongate shaft 110 and/or the proximal portion 112 of the elongate shaft 110 may include a stop feature 108 disposed proximate the proximal end of the elongate shaft 110. The stop feature 108 may have a radial extent greater than a radial extent of the elongate shaft 110 and/or the proximal portion 112 of the elongate shaft 110. In at least some embodiments, the stop feature 108 may be substantially rigid and/or inflexible. In some embodiments, the stop feature 108 may be assembled to and/or fixedly attached the elongate shaft 110, such as by welding, adhesive bonding, other suitable means. In some embodiments, the stop feature 108 may be integrally formed with the elongate shaft 110 as a unitary structure. In at least some embodiments, the stop feature 108 may be formed from the same material as the elongate shaft 110. In some embodiments, the stop feature 108 may be formed from a different material than the elongate shaft 110.

As seen in FIG. 2, the medical device system 100 may include a release wire 120 disposed within the lumen of the elongate shaft 110. A medical device 130 may be disposed proximate the distal end of the elongate shaft 110. The release wire 120 may be configured to releasably attach the medical device 130 to the distal end of the elongate shaft 110 in a first position, as seen in FIG. 2 for example. For simplicity, the medical device 130 is illustrated herein as a shape memory embolic coil, such as those used to treat aneurysms for example, but other suitable medical devices transported, delivered, used, released etc. in a similar manner are also contemplated, including but not limited to stents, embolic filters, replacement heart valves, occlusion devices, and/or other medical implants, etc. In some embodiments, the release wire 120 may be alternately and/or interchangeably referred to as a pull wire, an actuation wire, and/or a locking wire. The release wire 120 may generally be a solid wire or shaft, but may also be tubular in some embodiments. In some embodiments, the proximal portion 112 of the elongate shaft 110 may be fixedly attached to a proximal end of the release wire 120. In some embodiments, the stop feature 108 may be fixedly attached to the proximal end of the release wire 120. Some suitable but non-limiting materials for the release wire 120 and/or the medical device 130, for example metallic materials, polymer materials, composite materials, etc., are described below.

Returning to FIG. 1, the medical device system 100 may include an introducer sheath 140 slidably disposed over and/or on the elongate shaft 110. The introducer sheath 140 may include a proximal portion 142, a distal portion 144, and a stepped region 146 disposed between the proximal portion 142 and the distal portion 144. The proximal portion 142 of the introducer sheath 140 may be joined to the distal portion 144 of the introducer sheath 140 at the stepped region 146. In at least some embodiments, the proximal portion 142 of the introducer sheath 140 may include a necked region 148. As shown in FIG. 1, when initially packaged, the medical device system 100 may include the introducer sheath 140 disposed over the medical device 130 (not visible in FIG. 1) and/or the distal end of the elongate shaft 110. As such, the medical device 130 and/or the distal end of the elongate shaft 110 may be disposed within the distal portion 144 of the introducer sheath 140. So positioned, the introducer sheath 140 may hold and/or protect the medical device 130 prior to and/or during insertion into a microcatheter, as discussed herein. In at least some embodiments, the introducer sheath 140 and/or the distal portion 144 of the introducer sheath 140 may include a distal tip 141, which is described in more detail below.

As seen in FIG. 2, the proximal portion 142 of the introducer sheath 140 includes a lumen 143 having a radial extent greater than the radial extent of the stop feature 108. The distal portion 144 of the introducer sheath 140 may include a lumen 145 having a radial extent less than the radial extent of the stop feature 108. The proximal portion 142 of the introducer sheath 140 may include a necked region 148 having a radial extent less than the radial extent of the lumen 143 of the proximal portion 142 of the introducer sheath 140. The radial extent of the necked region 148 may be less than the radial extent of the stop feature 108.

In some embodiments, the medical device system 100 may include a microcatheter 190 including a lumen therein sized and configured to deliver the medical device 130 to a treatment site. In at least some embodiments, a distal end of the introducer sheath 140 may be configured to be disposed within a proximal end of the lumen of the microcatheter 190 to facilitate transfer and/or advancement of the elongate shaft 110 and/or the medical device 130 into the lumen of the microcatheter 190, as seen in FIG. 2. Accordingly, the introducer sheath 140 may be configured to guide the medical device 130 and/or the distal end of the elongate shaft 110 into the lumen of the microcatheter 190. The elongate shaft 110 and the medical device 130 may be slidably disposed within the lumen of the microcatheter 190. The elongate shaft 110 and/or the medical device 130 may be advanced through the lumen of the microcatheter 190 for deployment of the medical device 130 at a treatment site. In some embodiments, the microcatheter 190 may facilitate percutaneous delivery of the medical device 130 to a treatment site. Some suitable but non-limiting materials for the microcatheter 190, for example metallic materials, polymer materials, composite materials, etc., are described below.

Figure 3:
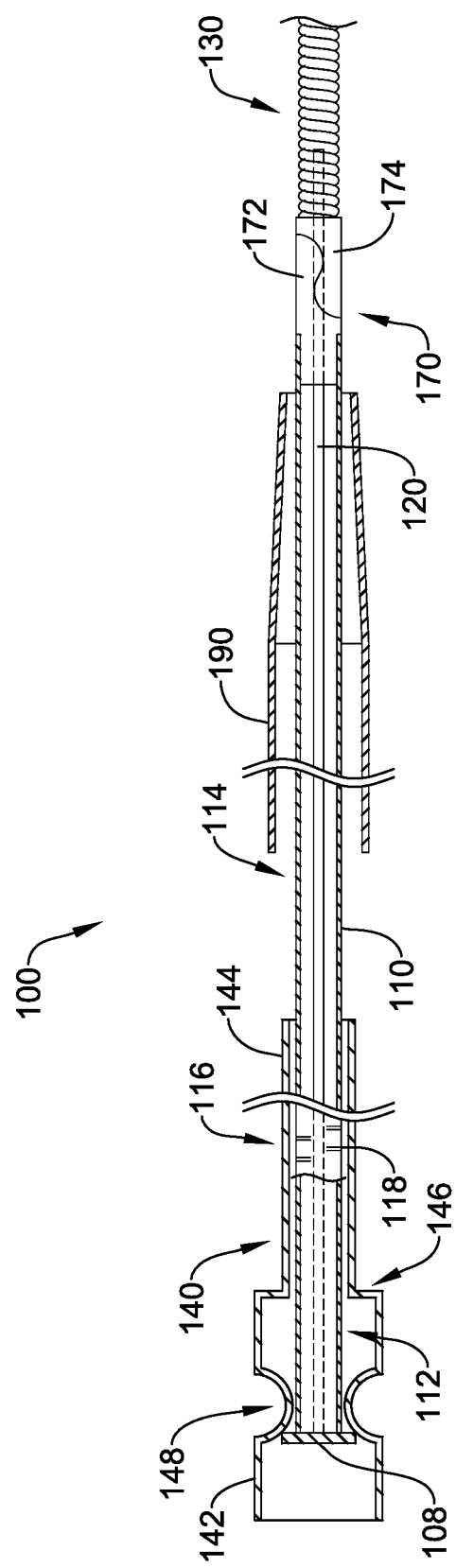
Figure 4:
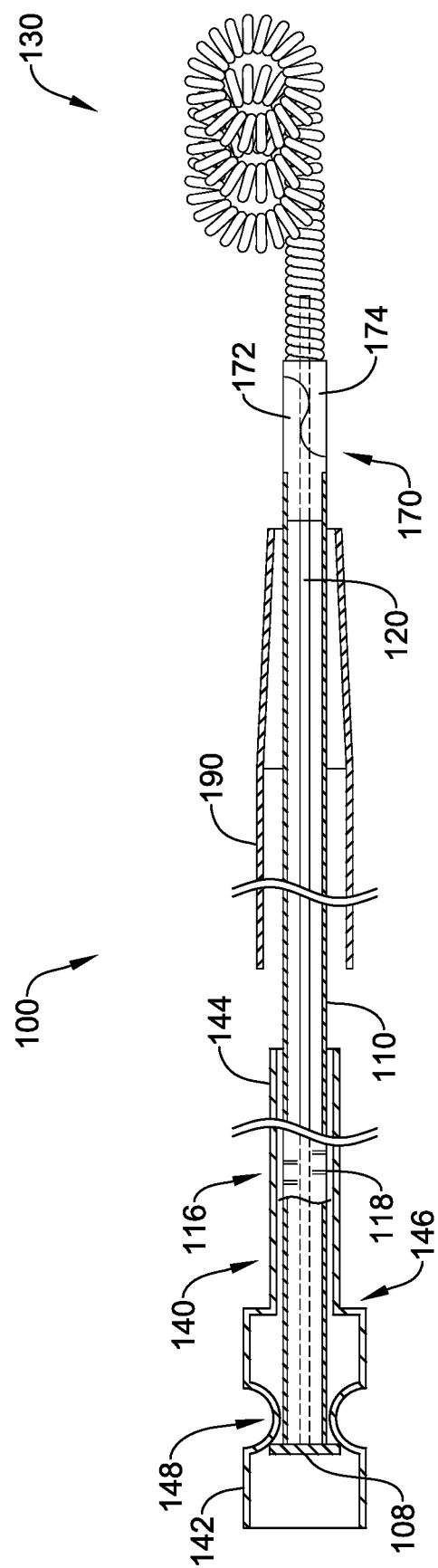

In some embodiments, a release mechanism 170 may releasably attach the medical device 130 to the distal end of the elongate shaft 110. In some embodiments, the elongate shaft 110 may include a first portion 172 of the release mechanism 170 fixedly attached to the distal end of the elongate shaft 110 and the medical device 130 may include a second portion 174 of the release mechanism 170 fixedly attached to a proximal end of the medical device 130. A distal end of the release wire 120 may slidably engage with the first portion 172 of the release mechanism 170 and the second portion 174 of the release mechanism 170, as seen in FIGS. 2-4. The release wire 120 may interlock the first portion 172 of the release mechanism 170 with the second portion 174 of the release mechanism 170 when the proximal portion 112 of the elongate shaft 110 is engaged with the distal portion 114 of the elongate shaft 110 and/or when the release wire 120 is in the first position. For example, when the proximal portion 112 of the elongate shaft 110 is disengaged and/or separated from the distal portion 114 of the elongate shaft 110 (e.g., FIG. 7), the release wire 120 may be translated in a proximal direction relative to the elongate shaft 110 to release the second portion 174 of the release mechanism 170 and/or the medical device 130 from the first portion 172 of the release mechanism 170 and/or the elongate shaft 110, as seen in more detail in FIG. 8. In at least some embodiments, the release wire 120 may be slidably disposed within the distal portion 114 of the elongate shaft 110, the first portion 172 of the release mechanism 170, and the second portion 174 of the release mechanism 170. Some suitable but non-limiting materials for the release mechanism 170, for example metallic materials, polymer materials, composite materials, etc., are described below.

FIG. 3 illustrates that after inserting the distal end of the elongate shaft 110 and/or the medical device 130 into the lumen of the microcatheter 190 and thereafter advancing the distal end of the elongate shaft 110 and/or the medical device 130 some distance into and/or through the microcatheter 190, the introducer sheath 140 may be retracted along and/or relative to the elongate shaft 110 until the stop feature 108 engages the necked region 148 of the proximal portion 142 of the introducer sheath 140. The necked region 148 may be configured to engage the stop feature 108 with the pre-defined break region 116 disposed between a proximal end of the introducer sheath 140 and a distal end of the introducer sheath 140. In at least some embodiments, the necked region 148 may be configured to engage the stop feature 108 with the pre-defined break region 116 disposed between a proximal end of the distal portion 144 of the introducer sheath 140 and a distal end of the distal portion 144 of the introducer sheath 140. For example, the necked region 148 may be configured to engage the stop feature 108 with the pre-defined break region 116 disposed between the stepped region 146 of the introducer sheath 140 and a distal end of the distal portion 144 of the introducer sheath 140 (e.g., within the distal portion 144). In FIG. 3, the medical device 130 is shown in a delivery configuration, wherein the medical device 130 is substantially aligned with, coaxial with, and/or colinear with the elongate shaft 110 and/or a central longitudinal axis of the elongate shaft 110. In at least some embodiments, the medical device 130 may be positioned and/or arranged in a substantially elongated configuration in the delivery configuration.

In some embodiments, the necked region 148 of the proximal portion 142 of the introducer sheath 140 may be at least partially flexible. As the medical device 130 is being advanced and/or deployed, the necked region 148 creates and/or provides tactile feedback to the user via increased resistance to movement of the introducer sheath 140 relative to the elongate shaft 110 as the stop feature 108 engages the necked region 148. Accordingly, the user will stop relative motion of the introducer sheath 140 until such time as release of the medical device 130 is desired. In this position and/or configuration, the distal portion 144 of the introducer sheath 140 may act as a strain relief for the elongate shaft 110, and for the pre-defined break region 116 in particular, thereby reducing stress upon the pre-defined break region 116 to prevent premature disengagement of the proximal portion 112 of the elongate shaft 110 from the distal portion 114 of the elongate shaft 110 and/or premature release of the medical device 130.

FIG. 4 illustrates the medical device system 100 of FIG. 3 after the medical device 130 has been shifted and/or actuated into a deployed configuration. In some embodiments, the medical device 130 may be shifted and/or actuated into the deployed configuration manually, such as by the use of selective electrical, chemical, and/or magnetic stimulation, a pull wire, etc. In some embodiments, the medical device 130 may be shifted and/or actuated into the deployed configuration automatically, such as by the use of shape memory materials or other suitable methods. For illustrative purposes only, the medical device 130 is shown in a helical deployed configuration. The medical device 130 may be shifted and/or actuated into the deployed configuration at any suitable and/or desired time after the medical device 130 has been advanced beyond the distal end of the microcatheter 190.

Figure 5:
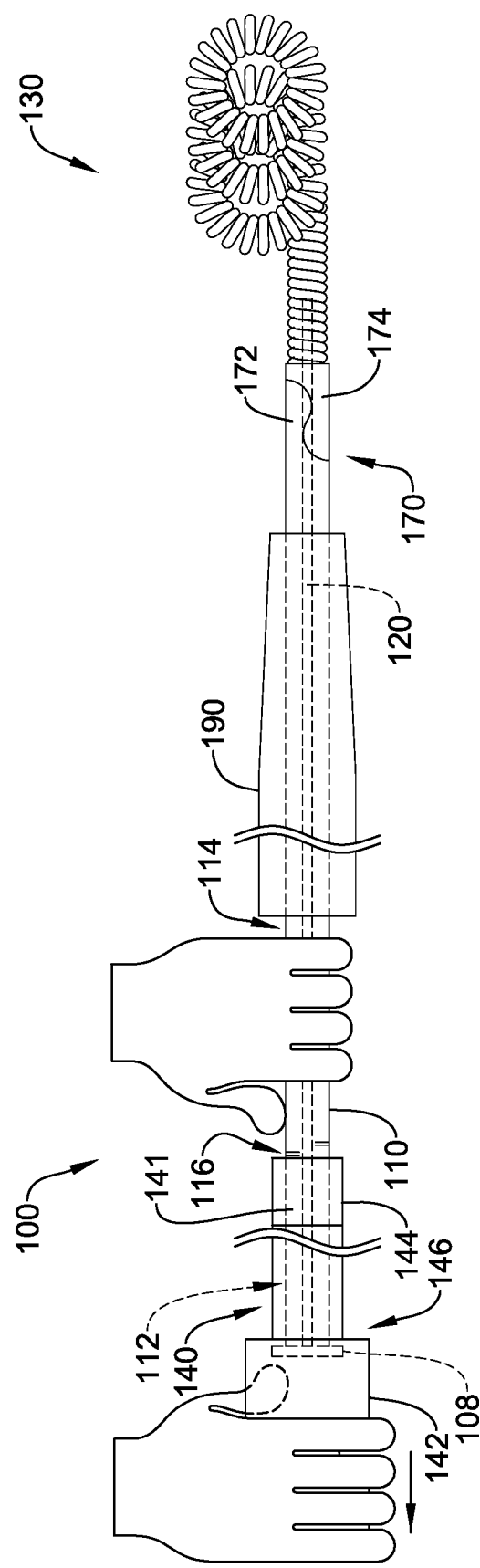
FIGS. 5-7 illustrate aspects of releasing the medical device from the medical device system.
Figure 6:
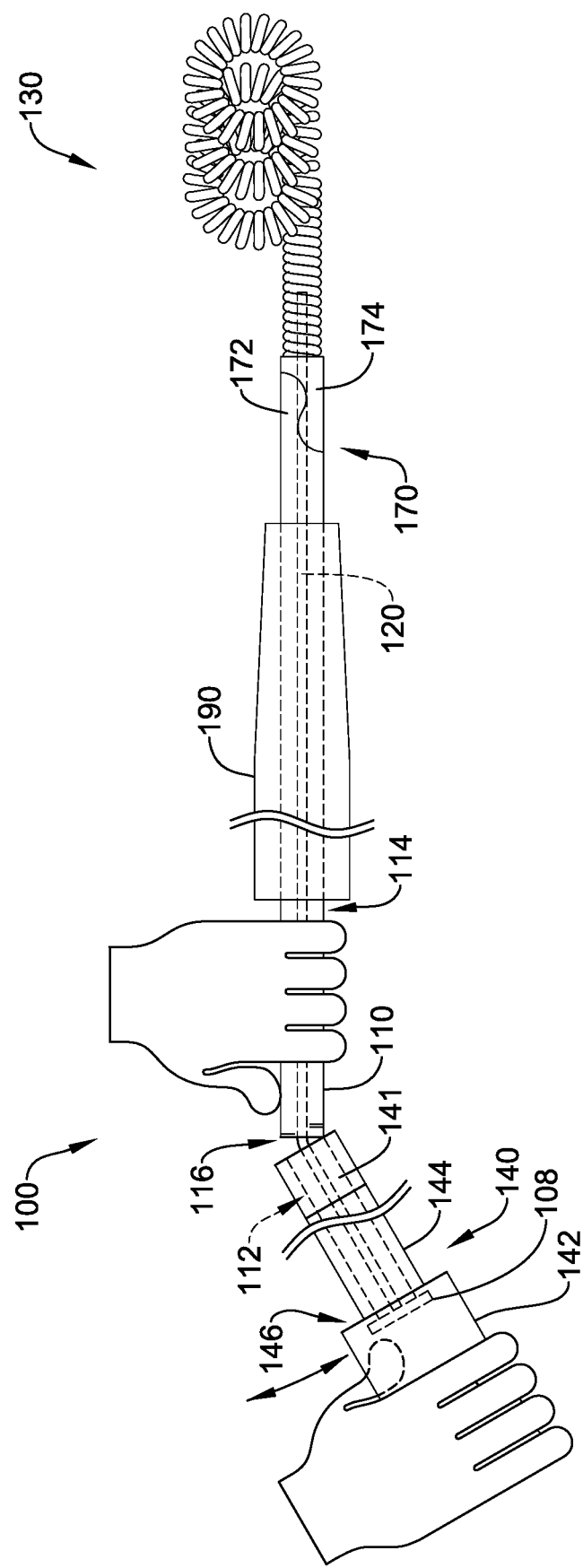
Figure 7:
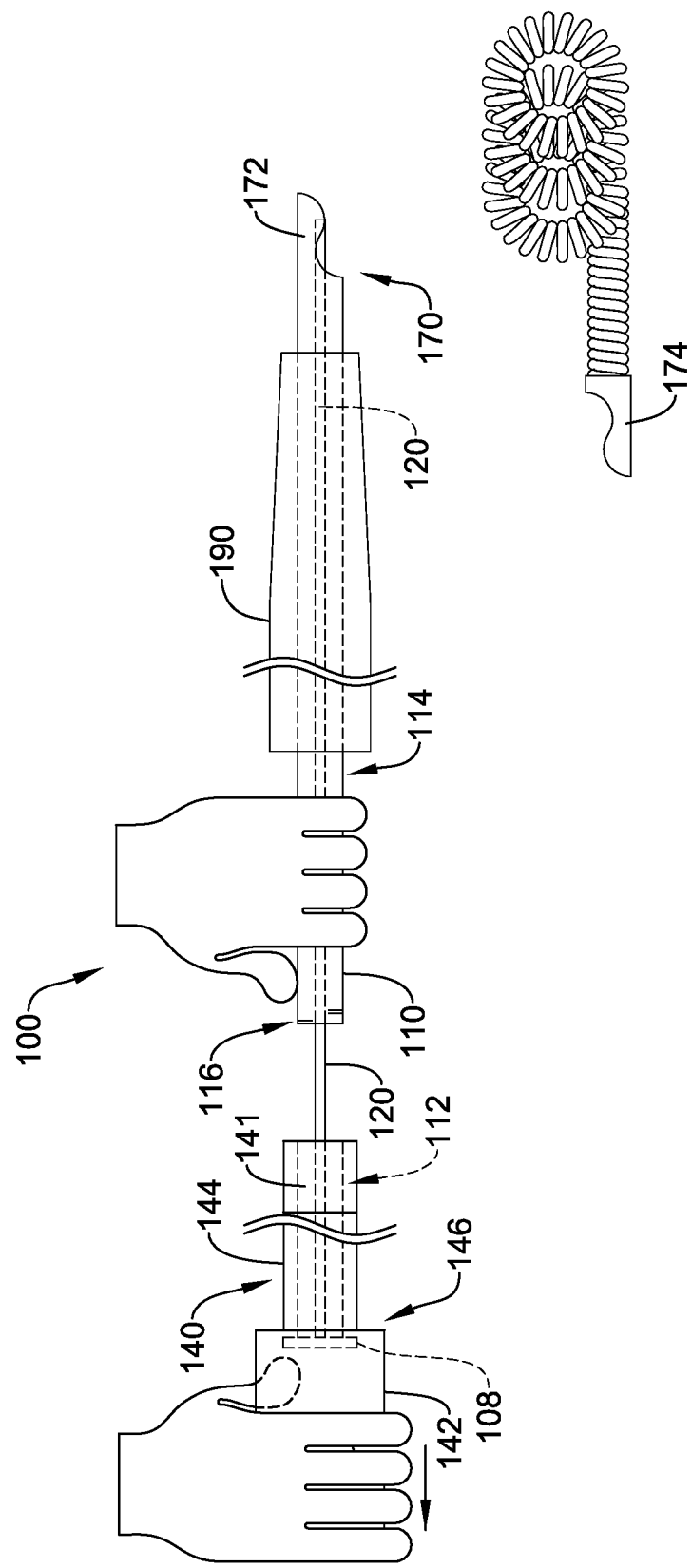

FIGS. 5-7 illustrate aspects of a method of releasing the medical device 130 from the elongate shaft 110. In use, the microcatheter 190 of the medical device system 100 may be inserted into a patient's anatomy and a distal end thereof guided and/or advanced to a location adjacent a treatment site. The medical device 130 disposed at the distal end of the elongate shaft 110 may be advanced through the microcatheter 190 to the treatment site. In some embodiments, the medical device 130 may be disposed within the lumen of the microcatheter 190 proximate to the distal end of the elongate shaft 110. In some embodiments, the medical device 130 may be disposed within the lumen of the microcatheter 190 proximate to the distal end of the elongate shaft 110 prior to use and/or prior to inserting the microcatheter 190 into the patient's anatomy. Deployment and/or release of the medical device 130 may be performed selectively depending upon the type of medical device and/or the desired treatment process or method. The elongate shaft 110 may have sufficient length that the proximal end of the elongate shaft 110 remains proximal of (e.g., extend proximally from) the microcatheter 190 when the medical device 130 is disposed distal of the microcatheter 190. In use, the elongate shaft 110 may have sufficient length to reach from the treatment site to a position outside of the patient where the medical device system 100 may be manipulated by the user.

When the user is ready to detach and/or release the medical device 130 from the elongate shaft 110 (e.g., when the medical device 130 has been positioned at the target site), the user may hold the distal portion 114 of the elongate shaft 110 to prevent movement of the distal portion 114 of the elongate shaft 110 and the user may hold the introducer sheath 140. Alternatively, the distal portion 114 of the elongate shaft 110 may be locked and/or held in a fixed position using a securement device such that a user's hand is not required to prevent movement of the distal portion 114 of the elongate shaft 110.

As seen in FIG. 5, the introducer sheath 140 may be moved proximally relative to the elongate shaft 110 by overcoming the resistance to movement provided by the necked region 148 of the proximal portion 142 of the elongate shaft 110. In at least some embodiments, the stop feature 108 may deflect the necked region 148 radially outward from the central longitudinal axis of the elongate shaft 110 and/or the introducer sheath 140 as the stop feature 108 moves and/or translates through the necked region 148. The introducer sheath 140 may be moved proximally relative to the elongate shaft 110 until the stop feature 108 engages the stepped region 146. At this point, the release wire 120 is still in the first position. In at least some embodiments, the stop feature 108 may prevent axial translation of the release wire 120 relative to the elongate shaft 110 and/or the medical device 130 prior to disengagement of the proximal portion 112 of the elongate shaft 110 from the distal portion 114 of the elongate shaft 110. The stepped region 146 may be configured to engage the stop feature 108 with the pre-defined break region 116 disposed at the distal end and/or the distal tip 141 of the introducer sheath 140.

In some embodiments, a portion of the pre-defined break region 116 may be disposed proximal to the distal tip 141 of the introducer sheath 140 and a portion of the pre-defined break region 116 may be disposed distal of the distal tip 141 of the introducer sheath 140. In some embodiments, the distal tip 141 of the introducer sheath 140 may stiffer and/or more rigid than a remainder of the introducer sheath 140 and/or the distal portion 144 of the introducer sheath 140. At a proximal-most position of the introducer sheath 140 relative to the elongate shaft 110, the stop feature 108 may be engaged with the stepped region 146, as shown in FIG. 5. At the proximal-most position of the introducer sheath 140 relative to the elongate shaft 110, the distal end and/or the distal tip 141 of the introducer sheath 140 may be disposed at the pre-defined break region 116 as described herein.

After moving the introducer sheath 140 proximally relative to the elongate shaft 110 to the proximal-most position of the introducer sheath 140 relative to the elongate shaft 110, the elongate shaft 110 is ready for the proximal portion 112 of the elongate shaft 110 to be disengaged from the distal portion 114 of the elongate shaft 110. Next, the user may move the introducer sheath 140 laterally relative to the elongate shaft 110 and/or the central longitudinal axis of the elongate shaft 110. The introducer sheath 140 may be configured to disengage the proximal portion 112 of the elongate shaft 110 from the distal portion 114 of the elongate shaft 110. Deflection of the introducer sheath 140 relative to the central longitudinal axis of the elongate shaft 110 at the proximal-most position of the introducer sheath 140 relative to the elongate shaft 110 induces and/or causes disengagement of the proximal portion 112 of the elongate shaft 110 from the distal portion 114 of the elongate shaft 110, as shown in FIG. 6. The user and/or the introducer sheath 140 may apply a moment around the pre-defined break region 116, wherein the distal tip 141 of the introducer sheath 140 may create and/or increase stress and/or strain within the pre-defined break region 116 of the elongate shaft 110. This moment, stress, and/or strain may cause a break to form in the elongate shaft 110 at the pre-defined break region 116, thereby disengaging the proximal portion 112 of the elongate shaft 110 from the distal portion 114 of the elongate shaft 110.

Disengaging the proximal portion 112 of the elongate shaft 110 from the distal portion 114 of the elongate shaft 110 permits the release wire 120 to axially translate and/or move relative to the distal portion 114 of the elongate shaft 110, the release mechanism 170, and/or the medical device 130. As such, the release wire 120 is translatable and/or movable to a second position when the distal portion 114 of the elongate shaft 110 is disengaged from the proximal portion 112 of the elongate shaft 110. With the release wire 120 in the second position, the medical device 130 may be detachable from the first portion 172 of the release mechanism 170 and/or the distal end of the elongate shaft 110.

Figure 8:
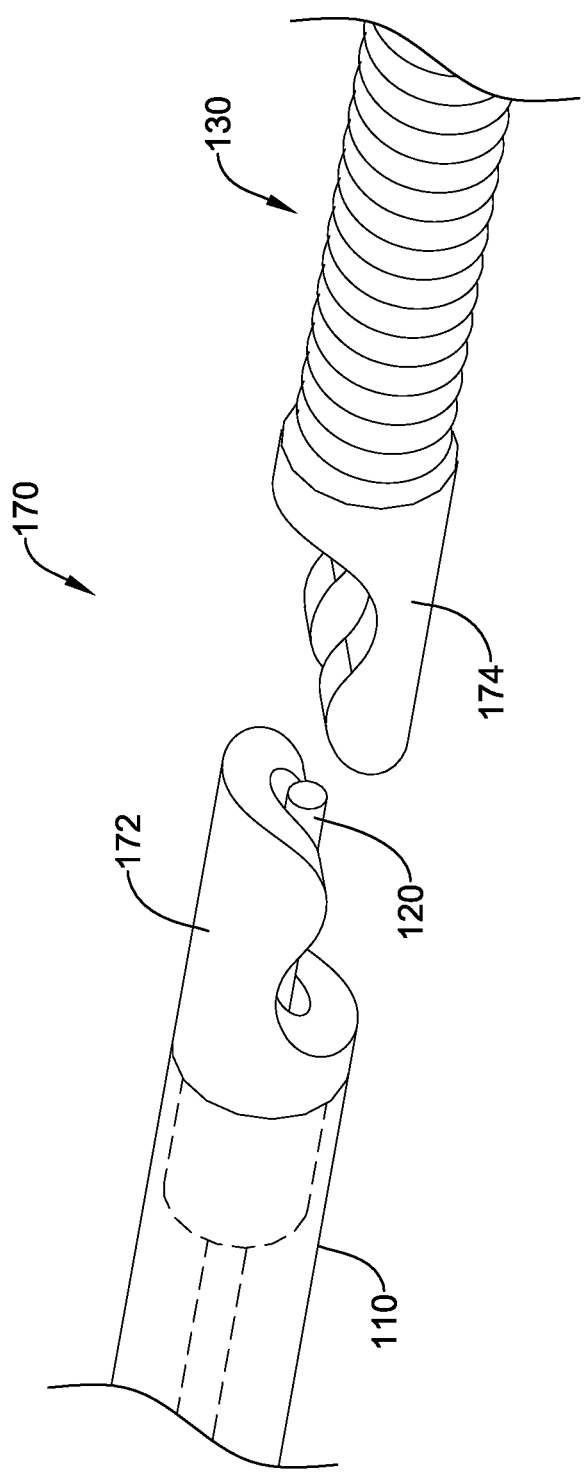
FIG. 8 illustrates an example release mechanism of the medical device system.

Accordingly, axial and/or proximal translation and/or movement of the introducer sheath 140 and/or the proximal portion 112 of the elongate shaft 110 relative to the distal portion 114 of the elongate shaft 110 may proximally retract the release wire 120 to the second position, thereby releasing the second portion 174 of the release mechanism 170 and/or the medical device 130 from the first portion 172 of the release mechanism 170 and/or the distal end of the elongate shaft 110, as shown in FIGS. 7-8.

Some benefits of the medical device system 100 may include, but are not limited to, a more robust pre-defined break region 116 and/or plurality of slits 118. In addition or alternatively, the user may not need to visually find and/or identify the pre-defined break region 116 during use. In addition or alternatively, the medical device system 100 and/or the elongate shaft 110 may be less sensitive to the exact positioning of the user's hands around the pre-defined break region 116 when preparing to disengage and/or during disengagement of the proximal portion 112 of the elongate shaft 110 from the distal portion 114 of the elongate shaft 110. In addition or alternatively, the medical device system 100 may require fewer or no visual identification elements on portions of the medical device system 100 disposed outside of the patient.

Figure 9:
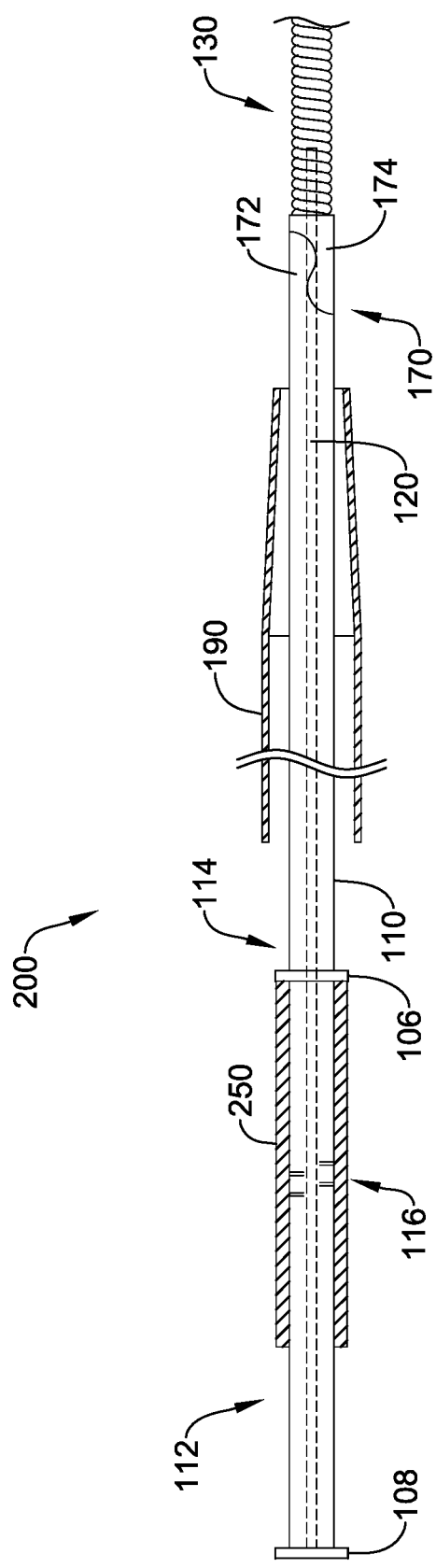
FIGS. 9-10 are partial cross-sectional views illustrating aspects of an alternative configuration of the medical device system.
Figure 10:
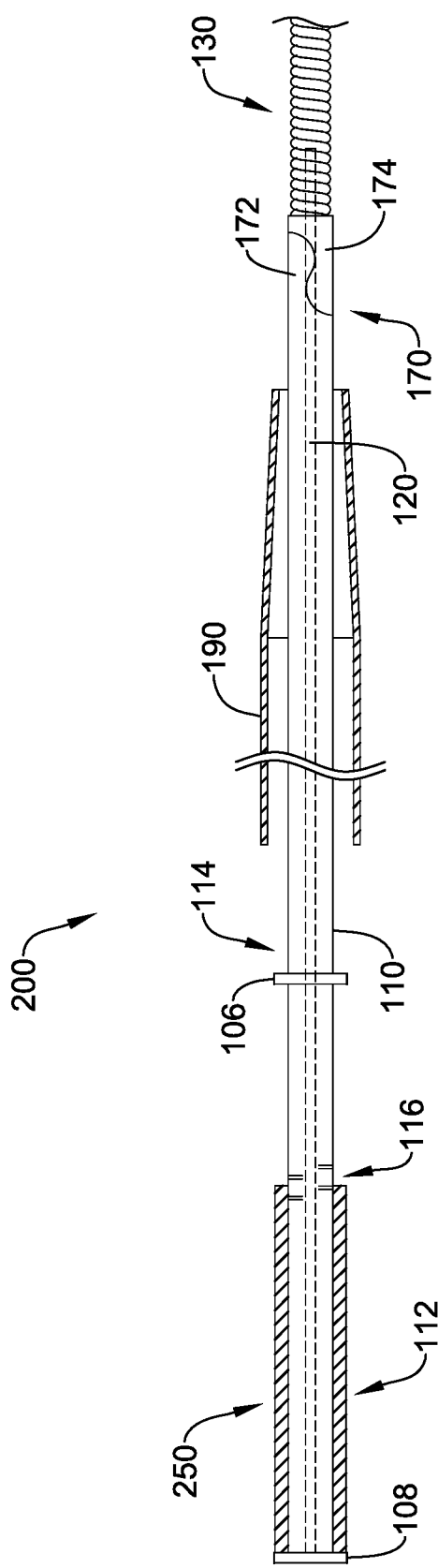

FIGS. 9-10 illustrate an alternative configuration of a medical device system 200, which may be similar to the medical device system 100 described herein in many ways, except as expressly disclosed. The medical device system 200 may include the elongate shaft 110, the release wire 120, the medical device 130, and the microcatheter 190 as described above with respect to the medical device system 100. In some embodiments, the medical device system 200 may include an introducer sheath configured to guide the elongate shaft 110 and/or the medical device 130 into the lumen of the microcatheter 190. Such an introducer sheath may or may not be captive and/or retained on the elongate shaft 110. In addition to the stop feature 108 described above, the elongate shaft 110 may include a second stop feature 106 disposed distal of the stop feature 108 and/or distal of the pre-defined break region 116.

A protective tube 250 may be slidably disposed on the elongate shaft 110 between the stop feature 108 and the second stop feature 106. The protective tube 250 may be held slidably captive and/or may be retained on the elongate shaft 110 by the stop feature 108 and the second stop feature 106. In some embodiments, the protective tube 250 may be configured to engage with the stop feature 108 and/or the second stop feature 106 in a way that prevents free movement of the protective tube 250 relative to the elongate shaft 110, such as a press fit, interference fit, or other suitable means of retention of the protective tube 250 against the stop feature 108 and/or the second stop feature 106. The protective tube 250 may be disposed over the pre-defined break region 116 in a first position, wherein the pre-defined break region 116 is disposed between a proximal end of the protective tube 250 and a distal end of the protective tube 250. The protective tube 250 may be configured to slide proximally relative to the elongate shaft 110 to a second position. The distal end of the protective tube 250 may be disposed at the pre-defined break region 116 in the second position. Some suitable but non-limiting materials for the protective tube 250, for example metallic materials, polymer materials, composite materials, etc., are described below.

When in the first position, as seen in FIG. 9 for example, the protective tube 250 may be configured to act as a strain relief for the elongate shaft 110, and for the pre-defined break region 116 in particular, thereby reducing stress upon the pre-defined break region 116 to prevent premature disengagement of the proximal portion 112 of the elongate shaft from the distal portion 114 of the elongate shaft and/or premature release of the medical device 130.

When the user is ready to detach and/or release the medical device 130 from the elongate shaft 110 (e.g., when the medical device 130 has been positioned at the target site), the user may hold the distal portion 114 of the elongate shaft 110 to prevent movement of the distal portion 114 of the elongate shaft 110 and the user may hold the protective tube 250. Alternatively, the distal portion 114 of the elongate shaft 110 may be locked and/or held in a fixed position using a securement device such that a user's hand is not required to prevent movement of the distal portion 114 of the elongate shaft 110.

As seen in FIG. 10, the protective tube 250 may be moved proximally relative to the elongate shaft 110 to the second position. The protective tube 250 may be moved proximally relative to the elongate shaft 110 until the stop feature 108 engages the protective tube 250 in the second position. At this point, the release wire 120 is still in its first position. In at least some embodiments, the stop feature 108 may prevent axial translation of the release wire 120 relative to the elongate shaft 110 and/or the medical device 130 prior to disengagement of the proximal portion 112 of the elongate shaft 110 from the distal portion 114 of the elongate shaft 110. The protective tube 250 may be configured to engage the stop feature 108 with the pre-defined break region 116 disposed at the distal end of the protective tube 250.

In some embodiments, a portion of the pre-defined break region 116 may be disposed proximal to the distal end of the protective tube 250 and a portion of the pre-defined break region 116 may be disposed distal of the distal end of the protective tube 250. In some embodiments, the distal end of the protective tube 250 may stiffer and/or more rigid than a remainder of the protective tube 250. At a proximal-most position of the protective tube 250 relative to the elongate shaft 110, the stop feature 108 may be engaged with the proximal end of the protective tube 250, as shown in FIG. 10. At the proximal-most position of the protective tube 250 relative to the elongate shaft 110, the distal end of the protective tube 250 may be disposed at the pre-defined break region 116 as described herein.

After moving the protective tube 250 proximally relative to the elongate shaft 110 to the proximal-most position of the protective tube 250 relative to the elongate shaft 110, the elongate shaft 110 is ready for the proximal portion 112 of the elongate shaft 110 to be disengaged from the distal portion 114 of the elongate shaft 110. Next, the user may move the protective tube 250 and/or the introducer sheath laterally relative to the elongate shaft 110 and/or the central longitudinal axis of the elongate shaft 110. The protective tube 250 and/or the introducer sheath may be configured to disengage the proximal portion 112 of the elongate shaft 110 from the distal portion 114 of the elongate shaft 110. Deflection of the protective tube 250 and/or the introducer sheath relative to the central longitudinal axis of the elongate shaft 110 at the proximal-most position of the protective tube 250 relative to the elongate shaft 110 may induce and/or cause disengagement of the proximal portion 112 of the elongate shaft 110 from the distal portion 114 of the elongate shaft 110. The user, the protective tube 250, and/or the introducer sheath may apply a moment around the pre-defined break region 116, wherein the distal end of the protective tube 250 may create and/or increase stress and/or strain within the pre-defined break region 116 of the elongate shaft 110. This moment, stress, and/or strain may cause a break to form in the elongate shaft 110 at the pre-defined break region 116, thereby disengaging the proximal portion 112 of the elongate shaft 110 from the distal portion 114 of the elongate shaft 110, similar to the medical device system 100 above.

The materials that can be used for the various components of the medical device system 100/200, the medical device 130, etc. (and/or other systems disclosed herein) and the various elements thereof disclosed herein may include those commonly associated with medical devices. For simplicity purposes, the following discussion makes reference to the medical device system 100/200, the medical device 130, etc. However, this is not intended to limit the devices and methods described herein, as the discussion may be applied to other elements, members, components, or devices disclosed herein, such as, but not limited to, the elongate shaft 110, the release wire 120, the introducer sheath 140, the release mechanism 170, the protective tube 250, etc. and/or elements or components thereof.

In some embodiments, the medical device system 100/200, the medical device 130, etc., and/or components thereof (such as, but not limited to, the medical device system 100/200, the medical device 130, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 100/200, the medical device 130, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 100/200, the medical device 130, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 100/200, the medical device 130, etc. to achieve the same result.

In some embodiments, a degree of Magnetic Resonance Imaging (MRI) compatibility is imparted into the medical device system 100/200, the medical device 130, etc. For example, the medical device system 100/200, the medical device 130, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 100/200, the medical device 130, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 100/200, the medical device 130, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 100/200, the medical device 130, etc., and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 100/200, the medical device 130, etc., and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 100/200, the medical device 130, etc., and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
an elongate shaft having a lumen extending to a distal end of the elongate shaft;
a medical device disposed proximate the distal end of the elongate shaft;
a release wire disposed within the lumen of the elongate shaft, wherein the release wire releasably attaches the medical device to the distal end of the elongate shaft;
wherein a proximal portion of the elongate shaft is configured to disengage from a distal portion of the elongate shaft; and
an introducer sheath slidably disposed over the elongate shaft, wherein the introducer sheath is configured to disengage the proximal portion of the elongate shaft from the distal portion of the elongate shaft;
wherein the elongate shaft includes a pre-defined break region formed in a wall of the elongate shaft;
wherein the elongate shaft includes a stop feature disposed proximate a proximal end of the elongate shaft;
wherein the introducer sheath includes a necked region configured to engage the stop feature with the pre-defined break region disposed between a proximal end of the introducer sheath and a distal end of the introducer sheath.

2. The medical device system of claim 1, wherein the proximal portion of the elongate shaft is fixedly attached to a proximal end of the release wire.

3. The medical device system of claim 1, wherein disengaging the proximal portion of the elongate shaft from the distal portion of the elongate shaft permits the release wire to axially translate relative to the elongate shaft.

4. The medical device system of claim 3, wherein axial translation of the proximal portion of the elongate shaft relative to the distal portion of the elongate shaft releases the medical device from the distal end of the elongate shaft.

5. The medical device system of claim 1, wherein the proximal portion of the elongate shaft is integrally formed with the distal portion of the elongate shaft.

6. The medical device system of claim 1, wherein the proximal portion of the elongate shaft is disposed proximal of the pre-defined break region and the distal portion of the elongate shaft is disposed distal of the pre-defined break region.

7. The medical device system of claim 1, wherein the pre-defined break region includes a plurality of slits formed in the wall of the elongate shaft.

8. The medical device system of claim 1, wherein the introducer sheath includes a stepped region configured to engage the stop feature with the pre-defined break region disposed at the distal end of the introducer sheath.

9. A medical device system, comprising:
an elongate shaft having a lumen extending to a distal end of the elongate shaft, wherein a proximal portion of the elongate shaft is configured to disengage from a distal portion of the elongate shaft;
a medical device disposed proximate the distal end of the elongate shaft;
a release wire disposed within the lumen of the elongate shaft, wherein the release wire releasably attaches the medical device to the distal end of the elongate shaft;
wherein the release wire is fixedly attached to the proximal portion of the elongate shaft;
an introducer sheath slidably disposed over the elongate shaft, wherein the introducer sheath is configured to disengage the proximal portion of the elongate shaft from the distal portion of the elongate shaft; and
a microcatheter configured to deliver the medical device to a treatment site, wherein the introducer sheath is configured to guide the medical device and the elongate shaft into a lumen of the microcatheter;
wherein the proximal portion of the elongate shaft includes a stop feature;
wherein the introducer sheath includes a proximal portion and a distal portion;
wherein the proximal portion of the introducer sheath includes a lumen having a radial extent greater than a radial extent of the stop feature;
wherein the distal portion of the introducer sheath includes a lumen having a radial extent less than the radial extent of the stop feature.

10. The medical device system of claim 9, wherein a distal end of the introducer sheath is configured to be disposed within a proximal end of the lumen of the microcatheter.

11. The medical device system of claim 9, wherein the proximal portion of the introducer sheath is joined to the distal portion of the introducer sheath at a stepped region.

12. The medical device system of claim 9, wherein the proximal portion of the introducer sheath includes a necked region having a radial extent less than the radial extent of the lumen of the proximal region of the introducer sheath.

13. The medical device system of claim 12, wherein the radial extent of the necked region is less than the radial extent of the stop feature.

14. A medical device system, comprising:
an elongate shaft including a pre-defined break region located along a length of the elongate shaft, the pre-defined break region separating a proximal portion of the elongate shaft from a distal portion of the elongate shaft;
wherein the proximal portion of the elongate shaft is formed with the distal portion of the elongate shaft as a unitary structure;
a medical device disposed proximate a distal end of the elongate shaft;
a release wire disposed within the elongate shaft, wherein the release wire is configured to releasably attach the medical device to the elongate shaft in a first position;
wherein the proximal portion of the elongate shaft is fixedly attached to a proximal end of the release wire; and
an introducer sheath slidably disposed over the elongate shaft, wherein the introducer sheath is configured to disengage the proximal portion of the elongate shaft from the distal portion of the elongate shaft;
wherein at a proximal-most position of the introducer sheath relative to the elongate shaft, a distal end of the introducer sheath is disposed at the pre-defined break region.

15. The medical device system of claim 14, wherein the release wire is translatable to a second position when the distal portion of the elongate shaft is disengaged from the proximal portion of the elongate shaft;
wherein in the second position, the medical device is detachable from the distal end of the elongate shaft.

16. The medical device system of claim 14, wherein deflection of the introducer sheath relative to a central longitudinal axis of the elongate shaft at the proximal-most position induces disengagement of the proximal portion of the elongate shaft from the distal portion of the elongate shaft.

* * * * *